(12) United States Patent
Bonne et al.

(10) Patent No.: US 6,911,894 B2
(45) Date of Patent: Jun. 28, 2005

(54) SENSOR PACKAGE FOR HARSH ENVIRONMENTS

(75) Inventors: Ulrich Bonne, Hopkins, MN (US);
Ernest Satren, Bloomington, MN (US)

(73) Assignee: Honeywell International Inc., Morristown, NJ (US)

( * ) Notice: Subject to any disclaimer, the term of this patent is extended or adjusted under 35 U.S.C. 154(b) by 0 days.

(21) Appl. No.: 10/128,775

(22) Filed: Apr. 22, 2002

(65) Prior Publication Data

US 2003/0107467 A1 Jun. 12, 2003

Related U.S. Application Data

(63) Continuation-in-part of application No. 09/656,694, filed on Sep. 7, 2000, and a continuation-in-part of application No. 09/368,621, filed on Aug. 5, 1999, now Pat. No. 6,322,247, which is a continuation-in-part of application No. 09/239,125, filed on Jan. 28, 1999, now Pat. No. 6,361,206, which is a continuation-in-part of application No. 09/207,165, filed on Dec. 7, 1998, now Pat. No. 6,184,773.

(51) Int. Cl.$^7$ .............................................. H01C 3/04
(52) U.S. Cl. ................... 338/25; 73/204.12; 73/204.13; 73/204.25
(58) Field of Search .................. 338/25, 28; 73/204.12, 73/204.13, 204.22, 204.25

(56) References Cited

U.S. PATENT DOCUMENTS

| | | | |
|---|---|---|---|
| 4,304,128 A | * 12/1981 | Hafner et al. ............ | 73/204.22 |
| 4,343,768 A | 8/1982 | Kimura | |
| 4,472,239 A | 9/1984 | Johnson et al. | |
| 4,478,076 A | 10/1984 | Bohrer | |
| 4,478,077 A | 10/1984 | Bohrer | |
| 4,501,144 A | 2/1985 | Higashi et al. | |
| 4,548,078 A | 10/1985 | Bohrer et al. | |
| 4,555,939 A | 12/1985 | Bohrer et al. | |
| 4,566,320 A | 1/1986 | Bohrer | |
| 4,571,608 A | 2/1986 | Johnson | |

(Continued)

FOREIGN PATENT DOCUMENTS

| | | | |
|---|---|---|---|
| JP | 3-261825 | * 11/1991 | |
| WO | 8700917 | * 2/1987 | |
| WO | WO 01-07903 A2 | 2/2001 | |
| WO | WO 01-11322 A1 | 2/2001 | |
| WO | WO 01/84087 A1 | 11/2001 | ........... G01F/1/684 |

OTHER PUBLICATIONS

Brooks Institute, "High Performance Metal Sealed Mass Flow Controller", Design Specification DS–5964, dated Nov., 1998, Hatfield, PA, pp. 1–4.

*Primary Examiner*—Karl D. Easthom
(74) *Attorney, Agent, or Firm*—Kris T. Fredrick; Kermit D. Lopez; Luis M. Ortiz

(57) ABSTRACT

A sensor can be configured to generally include a flow channel block having a flow channel formed therein, and a sensor chip for sensing fluid flow, wherein a fluid in the flow channel surrounds the sensor chip. Alternatively, the sensor chip can be fastened at one side to a substrate and on another side of the substrate to a core tube inserted into the flow channel. This core tube provides electrical insulation and corrosion protection to the sensor chip, reduces flow noise, (and by the non-intrusive nature of the measurement) essentially eliminates the risk of fluid leakage, and maintains the fluid super-clean and contamination-free while improving structural integrity for the thermal measurements derived from the sensor chip. The use of such a core tube configuration also can protect the sensor from corrosion, radioactive or bacterial contamination, overheating, or freeze-ups. Such a core tube configuration also enables the core tube to be detachable and disposable, without requiring the replacement of the more costly sensor chip with its electronics and calibration.

16 Claims, 7 Drawing Sheets

U.S. PATENT DOCUMENTS

| | | |
|---|---|---|
| 4,581,928 A | 4/1986 | Johnson |
| 4,587,105 A | 5/1986 | Bonne et al. |
| 4,624,137 A | 11/1986 | Johnson et al. |
| 4,651,564 A | 3/1987 | Johnson et al. |
| 4,682,503 A | 7/1987 | Higashi et al. |
| 4,683,159 A | 7/1987 | Bohrer et al. |
| 4,696,188 A | 9/1987 | Higashi |
| 4,706,061 A | 11/1987 | Johnson |
| 4,708,636 A | 11/1987 | Johnson |
| 4,739,657 A | 4/1988 | Higashi et al. |
| 4,794,048 A | 12/1988 | Oboodi et al. |
| 4,825,693 A | 5/1989 | Bohrer et al. |
| 4,829,818 A | 5/1989 | Bohrer |
| 4,856,328 A | 8/1989 | Johnson |
| 4,867,842 A | 9/1989 | Bohrer et al. |
| 4,885,938 A | 12/1989 | Higashi |
| 4,891,977 A | 1/1990 | Johnson et al. |
| 4,895,616 A | 1/1990 | Higashi et al. |
| 4,914,742 A | 4/1990 | Higashi et al. |
| 4,914,947 A | 4/1990 | Davidson |
| 4,966,037 A | 10/1990 | Sumner et al. |
| 5,081,866 A | 1/1992 | Ochiai et al. ............ 73/204.21 |
| 5,237,523 A | 8/1993 | Bonne et al. |
| 5,279,155 A | 1/1994 | Johnson et al. |
| 5,311,447 A | 5/1994 | Bonne |
| 5,410,916 A | 5/1995 | Cook |
| 5,462,525 A | 10/1995 | Srisathapat et al. |
| 5,684,253 A | 11/1997 | Bonne et al. |
| 5,852,239 A | 12/1998 | Sato et al. |
| 5,852,247 A | 12/1998 | Batey |
| 5,869,749 A | 2/1999 | Bonne et al. |
| 5,886,249 A | 3/1999 | Bonne et al. |
| 5,965,812 A | 10/1999 | Manaka |
| 6,023,969 A | 2/2000 | Feller |
| 6,079,264 A * | 6/2000 | Yamakawa et al. ...... 73/204.26 |
| 6,112,591 A | 9/2000 | Manaka |
| 6,169,965 B1 | 1/2001 | Kubisiak et al. |
| 6,184,773 B1 | 2/2001 | Bonne et al. |
| 6,223,593 B1 | 5/2001 | Kubisiak et al. |
| 6,308,553 B1 | 10/2001 | Bonne et al. |
| 6,322,247 B1 | 11/2001 | Bonne et al. |
| 6,336,361 B1 * | 1/2002 | Uramachi et al. ....... 73/204.22 |
| 6,361,206 B1 | 3/2002 | Bonne |

* cited by examiner

SENSOR PACKAGE FOR HARSH ENVIRONMENTS

This is a continuation-in-part of U.S. patent application Ser. No. 09/656,694, filed Sep. 7, 2000, entitled "Robust Fluid Flow and Property Microsensor Made of Optimal Material," which is a continuation-in-part of U.S. patent application Ser. No. 09/207,165, filed Dec. 7, 1998, entitled "Rugged Fluid Flow and Property Microsensor," now U.S. Pat. No. 6,184,773, and of U.S. patent application Ser. No. 09/368,621, filed Aug. 5, 1999, entitled "Microsensor Housing," now U.S. Pat. No. 6,322,247, which is a Continuation-in-Part of U.S. patent application Ser. No. 09/239,125, filed Jan. 28, 1999, entitled "Microsensor Housing," now U.S. Pat. No. 6,361,206. The content of the foregoing patent applications and patents are hereby incorporated by reference.

TECHNICAL FIELD

The present invention relates generally to sensors utilized to detect the quality and movement of fluids, in either gaseous or liquid form. The present invention also relates to thermal sensors of such fluids. The present invention additionally relates to thermal sensors implemented on silicon, glass, or other substrates in microstructure form. The present invention also relates to sensor packages for harsh environments.

BACKGROUND OF THE INVENTION

Flow sensors are utilized in a variety of fluid-sensing applications for detecting the movement of fluids, which may be in gaseous of liquid form. One type of flow measurement, for example, is based on thermal sensors, which can also be utilized to detect the property of a fluid. Thermal sensors may be implemented, for example, on silicon in microstructure form. For convenience sake, and without limitation, the term "flow sensor" can be utilized to refer to such thermal sensors. (See e.g. U.S. Pat. No. 6,322,247 FIGS. 10a–f, and U.S. Pat. No. 6,184,773, which are both incorporated herein by reference.). The reader will appreciate that such sensors may be also utilized to measure primary fluid properties such as temperature, thermal conductivity, specific heat (e.g. U.S. Pat. Nos. 5,237,523 and 5,311,447, which are both incorporated herein by reference.), and other properties; and that the flows may be generated through forced or natural convection.

A thermal-type flow sensor can be formed from a substrate that includes a heating element and one or more heat-receiving elements. If two such sensing elements are utilized, they can be positioned at the upstream and downstream sides of the heating element relative to the direction of the fluid (liquid or gas) flow to be measured. When fluid flows along the substrate, it can be heated by the heating element at the upstream side and the heat can then be transferred non-symmetrically to the heat-receiving elements on either side of the heating element. Since the level of non-symmetry depends on the rate of gas flow, and that non-symmetry can be sensed electronically, such a flow sensor can be used to determine the rate and the cumulative amount of the fluid flow.

Such flow sensors generally face potential degradation problems when exposed to harsh (e.g., contaminated, dirty, condensing, etc.) fluids, including gases or liquids that can "stress" the sensor via corrosion, radioactive or bacterial contamination, overheating, deposits or freeze-ups. The sensitive measurement of the flow, or pressure (differential or absolute) of "harsh" gases or liquids that can stress, corrode, freeze-up, or overheat the sensing elements is a challenge that is either unmet or met at great expense. Among the solutions proposed previously are passivation with the associated desensitization of the sensor, heaters to raise the temperature of gaseous fluids to be measured to avoid condensation or freeze-ups (or coolers to prevent overheating) at the expense of sensor signal degradation, cost increase and possible fluid degradation, or filters to remove objectionable particulate matter. Frequent cleaning or replacement and recalibration of the sensors are additional, but costly, solutions. Sensitive, membrane-based differential pressure sensors can be protected against contamination because no flow is involved, but they are less sensitive and more expensive than thermal microsensors, in addition to not being overpressure proof.

The measurement of liquid flow via thermal microsensors, especially of electrically conductive fluids, thus presents challenging problems in terms of electrical insulation, flow noise, chip corrosion, potential for leaks or structural integrity of the flow channel, and thermal measurement. The electrical contacts to the sensor chip generally should be insulated from each other so the resistance to electrical leakage is above approximately 20 M$\Omega$ to avoid interference with the sensing function. Some $Si_3N_4$ passivation films, for example, have pinholes; spin-on coatings of compounds that form glass or Teflon® films upon curing have not shown insulation beyond a few days of contact with salt water. (Note that Teflon® is a registered trademark of the E. I. Du Pont De Nemours & Company Corporation of 101 West 101 West $10^{th}$ St., Wilmington, Del. 19898.) Even potting the wire-bonds in highly cross-linked epoxy led to either resistances dropping to, for example, 30M$\Omega$ and/or bond breakage if the epoxy became too brittle due to excessive cross-linking and/or thermal cycling. Additionally, the odd shape of the flow channel above the chip causes extra turbulence and corresponding signal noise. Another approach to providing electrical insulation for the electrical contacts and leadout wires is to move them out of the fluid-flow channel and contact area; however, such sidewise displacement adds real estate to the chip size and therefore to its cost.

Regarding structural integrity, a sensitive 1 $\mu$m-thick flow sensing membrane can easily break as a result of the stronger viscous and inertial forces that a liquid can exert on it. Such breakage has even been observed in cases of sharp gaseous pressure or flow pulses. Finally, with respect to thermal measurement issues, the heater temperature rise typically permissible in liquids (e.g., $\leq 20°$ C.) is much smaller than the one typically utilized in gases (e.g., 100–160° C.). The resulting, relatively small signal causes more significant increases in the effect of composition-, sensor- material- and temperature-dependent offsets, which can cause significant errors in the sensor flow readouts.

Based on the foregoing, the present inventors have concluded that the solution to the aforementioned problems lies appropriately in the "smart" application onto the sensing chip of a film that is strong enough to function as a protective barrier to the transfer of electrical charges and of molecular mass transfer but can be thin enough to enable transfer of heat to allow thermal measurements. The films may be fashioned of materials composed of inorganic compounds (even metals) or of hydrophobic or hydrophilic polymeric materials, as explained in further detail herein, which can result in operational flow sensors of high reliability, no electrical leakage, no fluid leakage by virtue of the non-intrusive character of the flow measurement, no corrosion, no fluid contamination, reduced flow noise and significantly reduced offset and drift problems.

BRIEF SUMMARY OF THE INVENTION

The following summary of the invention is provided to facilitate an understanding of some of the innovative features unique to the present invention and is not intended to be a full description. A full appreciation of the various aspects of the invention can be gained by taking the entire specification, claims, drawings, and abstract as a whole.

It is one aspect to provide an improved sensor utilized in the detection of the quality of fluids, including gas and liquid.

It is yet another aspect of the present invention to provide an improved thermal sensor utilized to measure the quality or property of fluids, be they gas or liquid.

It is still another aspect of the present invention to provide an improved thermal sensor that can be implemented on silicon, glass, or other substrates in microstructure form.

It is yet another aspect of the present invention to provide an improved sensor package for sensing harsh and corrosive fluids.

It is yet another aspect of the present invention to provide an improved sensor package for sensing pure or super-clean fluids, such that their contact with the sensor does not result in any detectable contamination of the fluid. This improvement results from the non-intrusive character of this sensing approach.

An apparatus is disclosed herein for detecting liquid flow in what may generically be referred to as a "harsh environment." A sensor can be configured to generally include a flow channel block having a flow channel formed therein. Such a sensor can also include a sensor chip for sensing fluid flow. The flowing fluid to be sensed generally surrounds the sensor chip. The sensor additionally includes a substrate fastened to the sensor chip and contacted by at least one bonding element and a molded core tube inserted into the flow channel of the flow channel block, which thereby reduces flow noise and potential corrosion, improves electrical insulation, structural integrity and thermal measurements thereof derived from the sensor chip. The bonding element can be configured to comprise one or more front wire bonds (FWBs) and/or through-the-wafer (TTW) contacts.

The molded core tube can be formed from a polymeric material, such as Teflon®, or other materials, such as glass, quartz, sapphire and/or metal, such as, for example, stainless steel. The molded core tube generally comprises a wall thickness that removes a surface of the sensor chip from direct contact with a fluid flowing through the molded core tube by a distance corresponding to the wall thickness, thereby desensitizing the sensor to fluid flow variations. Additionally, this tube wall thickness in contact with the sensor chip combines a high dielectric strength and chemical inertness with properties such as hydrophobic, hydrophilic and lipophilic as needed. Such properties may be realized with inorganic or organic materials. Note that as utilized herein the term fluid can be meant generally to refer to a gas or liquid. Thus, sensor packages disclosed herein can be utilized to measure the quality or property of a gas or a liquid.

The film can be enlarged to comprise a potting or molding compound associated with the bonding elements, whereby the molded core tube generally shapes the potting compound. The film itself may be formed from a material such as, for example, an epoxy material. Also, the molded core flow channel can be configured to include a constriction in a cross section of the molded core tube at the sensor chip to optimize performance thereof. The molded core flow channel and the substrate can be replaced by a flat film, which can be wrapped or shrunk about a header and sealed by an O-ring to provide sensor capabilities thereof. The flow tube is generally configured from a flow channel block and can be a disposable flow tube. Additionally, the sensor can be associated and/or integrated with a heat sink mechanism for heat sinking a reference resistance and/or temperature sensor associated with above flow sensor so that the flow sensor does not increase in temperature and drive an associated heater temperature to a point where a fluid flowing through the flow channel boils.

The sensor features a flat, passivated, top surface overlying the heater and sensor elements to provide appropriate electrical isolation. Further, the die, with its through-the-wafer interconnections, eliminates the need for bonding wires with their attendant problems as discussed above. In order to withstand a wide range of pressure levels and operate in harsh environments, the die structure is configured to be very robust. The die is made up of materials that have very low thermal conductivity, thus eliminating the possibility of undesired thermal signal shorts. For example, the die can be fabricated using various glass materials, alumina, or combinations of such materials.

The ability to perform high mass flux sensing operations is largely dependent upon the physical characteristics of the sensor. Most importantly, low thermal conductivity of the die substrate is necessary in order to create a sensor capable of operating in these high mass flux sensing situations. By minimizing the thermal conductivity, interference with sensor heating/cooling effects will be minimized and the sensing capabilities are enhanced. Specifically, the characteristics of the die substrate materials will control the proper route of heat transfer, avoiding transfer through the die substrate from the heater to the sensors. Various materials can provide this characteristic. Historically, silicon nitride of a microbridge sensor chip has been used to provide certain levels of thermal conductivity, while also being easily manufactured. However, its fragility prevents is use in harsh environments.

A more optimum material that exhibits the desired characteristic is glass. Glass, however, has not been previously used because it has not been easily micromachined. That is, it is difficult to form the required structures using glass. Another potential substrate material is alumina, which is widely used for electronics packaging and can be machined to serve as substrate with some desirable characteristics. One undesirable feature, however, is its high thermal conductivity, which would severely reduce the sensitivity of the sensor chip.

Recent developments in glass materials, including photosensitive glass and pyrex, have shown that micromachining is possible and extremely effective. Consequently, this material can now provide an alternate die substrate for a micromachined flow and property sensor. The present invention exploits the characteristics of glass (photosensitive glass, fused silica, etc.) or alumina materials to produce a flow and property sensor with optimized physical characteristics. Providing a glass based sensor in a Microbrick™ structure or microfill structure consequently enables the fabrication of a rugged sensor for sensing liquid properties or high mass flux fluid flow, without pressure-stress-induced error signals.

Due to the recent developments in glass, the use of this material as a die substrate generally reduces the amount of structural machining necessary. More specifically, the substrate can now be fabricated in a Microbrick™ structure or microfill structure, which has a substantially solid structure. In this type of sensor die, the heating and sensing elements are placed directly on the substrate and no further processing or structuring is required beneath those elements. Consequently, the substrate itself is continuous beneath the sensing elements creating a more robust sensor die. The characteristics of the glass substrate material allow this Microbrick™ structure to be effectively used in harsh environments.

BRIEF DESCRIPTION OF THE DRAWINGS

The accompanying figures, in which like reference numerals refer to identical or functionally-similar elements throughout the separate views and which are incorporated in and form part of the specification, further illustrate the present invention and, together with the detailed description of the invention, serve to explain the principles of the present invention.

DETAILED DESCRIPTION OF THE INVENTION

The particular values and configurations discussed in these non-limiting examples can be varied and are cited merely to illustrate preferred embodiments of the present invention and are not intended to limit the scope of the invention.

The present invention is related to the design and fabrication of the electrical insulation for electrical contacts to sensor chips using either front-wire-bond (FWB) or through-the-wafer (TTW) contacts of certain thermal flow microsensors or of environmental sensors in general. The present inventors previously insulated Au-wires and Au-pads of FWB sensor chips via materials, such as, for example, dip-coatings, dip-coatings with or without alumina thin-film undercoating, $Si_3N_4$, flowable sealants, solvent-resistant sealant with fluoro-silicon, and epoxies. Insulation based on such materials has been attempted as defined generally by the resistances between the sensing elements and the liquid (e.g., salt water) in a flow tube. Such resistances, however, are unacceptable if $\leq 20$ M$\Omega$. The invention described herein thus introduces a unique solution for solving such problems.

As will be explained in further detail herein, by potting insulating material (e.g., epoxy) around a core-mold of Teflon® wire or pipe of 0.010 to 0.060" OD, which may or may not be removed after curing, and using for example, a robust Microbrick® or an epoxy-back-filled microbridge, the aforementioned problems can be essentially eliminated. (Note that Microbrick® is a registered trademark of Honeywell International, Inc. of Morristown, N.J.) The increased thickness of the insulating "layer", relative to a dip-coat for example, causes the intrusion of fluids (e.g., water) and other conductive materials, such that their contribution to electrical conduction in the polymer becomes negligible. A straight and smooth flow channel, which can reduce turbulence and flow noise, thus replaces the odd flow channel spaces located above previously utilized sensor chips.

Replacing an unprotected microbridge by a Microbrick® chip can eliminate breakage due to fluid-generated forces. Note that the utilization of a Microbrick® chip or other such devices are not considered limiting features of the present invention but are mentioned herein for illustrative and general edification purposes only. The increased insulation thickness enables the application of larger voltages to the sensor heating elements, which raises the heater temperature (which may or may not be in direct contact with the liquid) and leads to larger output signals. As a result, heater resistance drift, and temperature-, fluid-type-, sensor-asymmetry-, and electronics-dependent offsets are less prominent.

Figure 1:
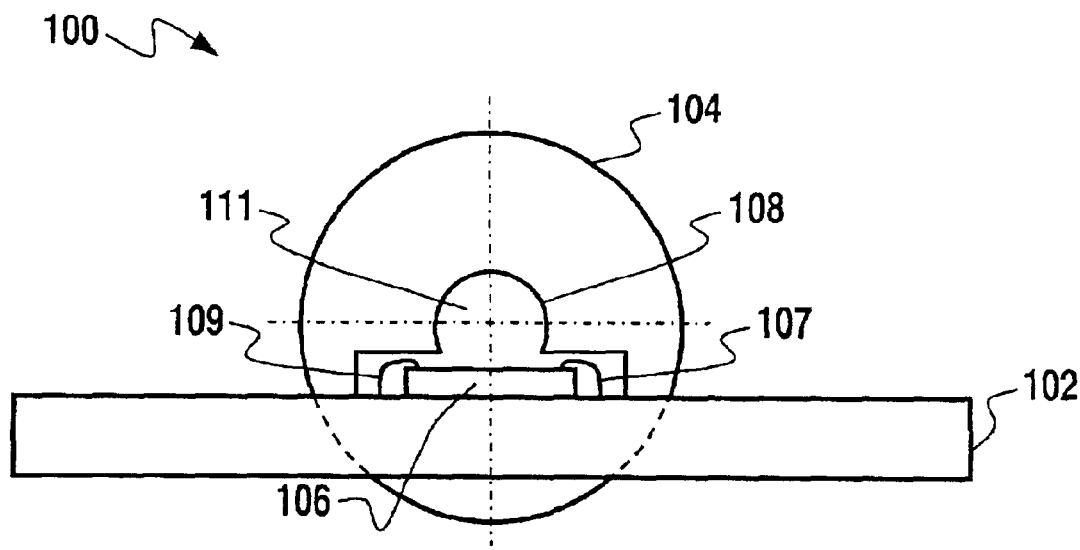
FIG. 1 illustrates a prior art cross-sectional view of a flow channel block, which may be modified and improved in accordance with a preferred embodiment of the present invention.

FIG. 1 illustrates a prior art cross-sectional view 100 of a plastic flow channel block 104, which may be modified and improved in accordance with a preferred embodiment of the present invention. FIG. 1 further illustrates a sensor chip 106 which is fastened or in communication with a substrate 102. The substrate 102 can support electrical I/O lead-outs, which may in turn be connected or bonded to various elements on chip 106 via "front wire bonds" (FWBs) 107 or "through-the-wafer" (TTW) contacts (not shown). A top flow channel 111 with an appropriate opening for the chip can then be fastened over the sensing chip 106. Ideally, care should be exercised so as not to spill excess adhesive into the path intended for the fluid. Thus, view 100 represents a drawing of a microsensor, prior to the introduction of the "core mold" concept of the present invention, as explained in further detail herein.

Figure 2:
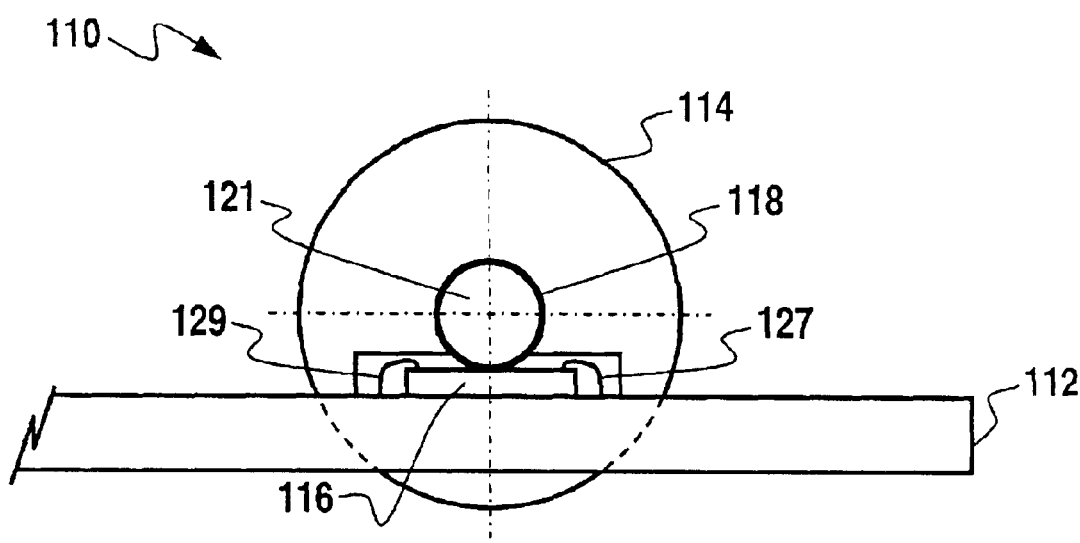
FIG. 2 depicts a cross sectional view of an improved flow channel block with an inserted core tube, in accordance with a preferred embodiment of the present invention.

FIG. 2 depicts a cross sectional view 110 of an improved flow channel block 104 with an inserted core tube 118, in accordance with a preferred embodiment of the present invention. FIG. 2 additionally illustrates a sensor chip 116 and a substrate 112. Flow channel block 114, which is analogous to flow channel block 104 of FIG. 1, now possesses an inserted core tube 118, in accordance with a preferred embodiment of the present invention. Substrate 112 may be composed of, for example, alumina, PCB, glass, or other substrate-type materials. Substrate 112 of FIG. 2 is generally analogous to substrate 102 of FIG. 1. Note that the term "substrate" as utilized herein can refer to a "substrate" or a "substrate board." The composition of the substrate is discussed further below. The flow channel block 114 is also generally analogous to flow channel block 104, with the exception that core tube 118 has been added to block 114. This facilitates the process of fastening flow channel block 114 to an "alumina" substrate 112.

The inserted core tube 118 is not pulled out but is maintained in place to provide the above-discussed advantages. Note that the wall thickness of inserted core tube 118 removes the surface of sensing chip 116 from direct contact with the fluid by a distance corresponding to that thickness, thus desensitizing the sensor to flow changes, which is the price paid for the other benefits mentioned above. Additionally, it is important to note that flow channel block 114 may be configured in the shape of a tube, thereby functioning as a flow tube. Flow channel block 114 thus may form a flow tube.

It can be appreciated by those skilled in the art, however, that flow channel block 114 may be configured in the form of other shapes, such as for example, a triangular-, square-, rectangular-shaped flow channel block, half-circles, or various other geometric shapes. Thus, the shape of flow channel block 114 can be an arbitrary design choice and is not considered a limiting feature of the present invention. Additionally, it can be appreciated that flow channel block 114 can be formed from a variety of materials, including, but not necessarily only, plastic.

Substrate 112 can support electrical I/O lead-outs, which may in turn be connected to various elements on sensor chip 116 via "front wire bonds" (FWBs) 127 and 129 illustrated in FIG. 2. Similarly, FWBs 107 and 109 are depicted in FIG. 1. Additionally, bonding elements can be configured as through-the-wafer (TTW) contacts, which are not illustrated in FIGS. 1 and 2. Flow channel block 114 can then be fastened over sensing chip 116 and substrate 112. Ideally, care should be exercised so as not to spill excess adhesive into the path intended for the fluid in FIG. 1. In FIG. 2, core tube 118 can prevent such spills and generally surrounds channel 121 through which a fluid may flow. Note that if core tube 118 is removed from flow channel block 114, channel 121 can be left in place after core tube 118 is removed from molding surrounding core tube 118. In this sense, core tube 118 may also be referred to as a "molded core tube."

The proper use of such a core tube can thus reduce flow noise, sensitivity, and the risk of contamination of superclean fluids, fluid leakage, chip corrosion and leakage potential, while improving electrical insulation, structural integrity and thermal measurements thereof derived from an associated sensor chip (e.g., sensor chip 116). Such a core tube can also be used to shape and mold an inner flow channel, which can be removed after curing of the molding compound. The flow sensor can then regain flow sensitivity and maintain low "flow noise" but may lose some chip corrosion protection, fluid and electrical leakage prevention, fluid contamination, non-intrusiveness and structural integrity.

Again, referencing FIG. 2, the substrate 112 can be comprised of alumina, mullite, or other known materials having coefficient of thermal expansion (CTE) suitably matched to the microsensor die. Silicon is often considered a very effective microsensor body material because it can be easily machined/processed using several well known silicon processing techniques. In certain applications, such as very high mass flux fluid flow sensing and high pressure applications, such silicon supported structures as microridges or mciromembranes do have certain disadvantages however. Specifically, the thermal isolation characteristics of silicon would limit structural and operational characteristics of a sensor if built directly on silicon. In order to deal with these thermal characteristics, the microsensor body of a silicon based sensor is configured in a micromembrane type structure, so as to limit the thermal mass below the heater and sensing elements. Obviously, this limits the physical strength of a silicon based sensor. In addition, this micromembrane configuration is not suitable for high mass flux sensing because its output signal saturates before reacting high flux levels.

In order to effectively operate in harsh environments, the flow sensor must be structurally robust. What is needed is a sensor robust enough to withstand high pressures due to sources (such as high pressure pulses, ultrasonic cleaning, and water hammer). In order to sense high mass flux flow rates, it is also necessary to have a substrate material with an appropriately low thermal conductivity (preferably $\leq 1.5$ W/(mK)). Certain glass materials provide better thermal isolation characteristics (than silicon), thus increasing the sensing capabilities of the above-outlined micromachined flow and property sensor. The use of glass also allows for a more robust physical structure to be used. These various characteristics result in a more versatile sensor, which can be used in multiple applications. Furthermore, as outlined below, certain techniques provide for effective micromachining of glass based substrates.

The use of glass as a microsensor body material provides multiple features which enhance the capabilities of the sensor. These features include: (1) the automatic electrical insulation for through-the-wafer contacts, (2) lower thermal conductivity than silicon, (3) environmental ruggedness needed to withstand pressure pulses as for sensing liquids, and (4) the ability to use a structurally robust sensor body configuration. Furthermore, the glass based sensor meets all requirements for chemical inertness, corrosion resistance, and biocompatability.

As mentioned above, glass provides inherent electrical isolation between various contacts. This is compared with a silicon based sensor where electrical isolation is achieved by incorporating silicon dioxide layers on the substrate unless more costly silicon wafers are used that are grown to be slightly insulating. Obviously, this eliminates one layer of material and one necessary processing step. This is particularly beneficial as the step of growing oxide is time consuming and done at fairly high temperatures.

While the sensor of the present invention can be implemented as glass-based sensor, it is understood that other materials having appropriate physical characteristics could also be used. For example, the substrate can be manufactured out of other materials including both glass or silicon or alumina or ceramic.

Figure 3:
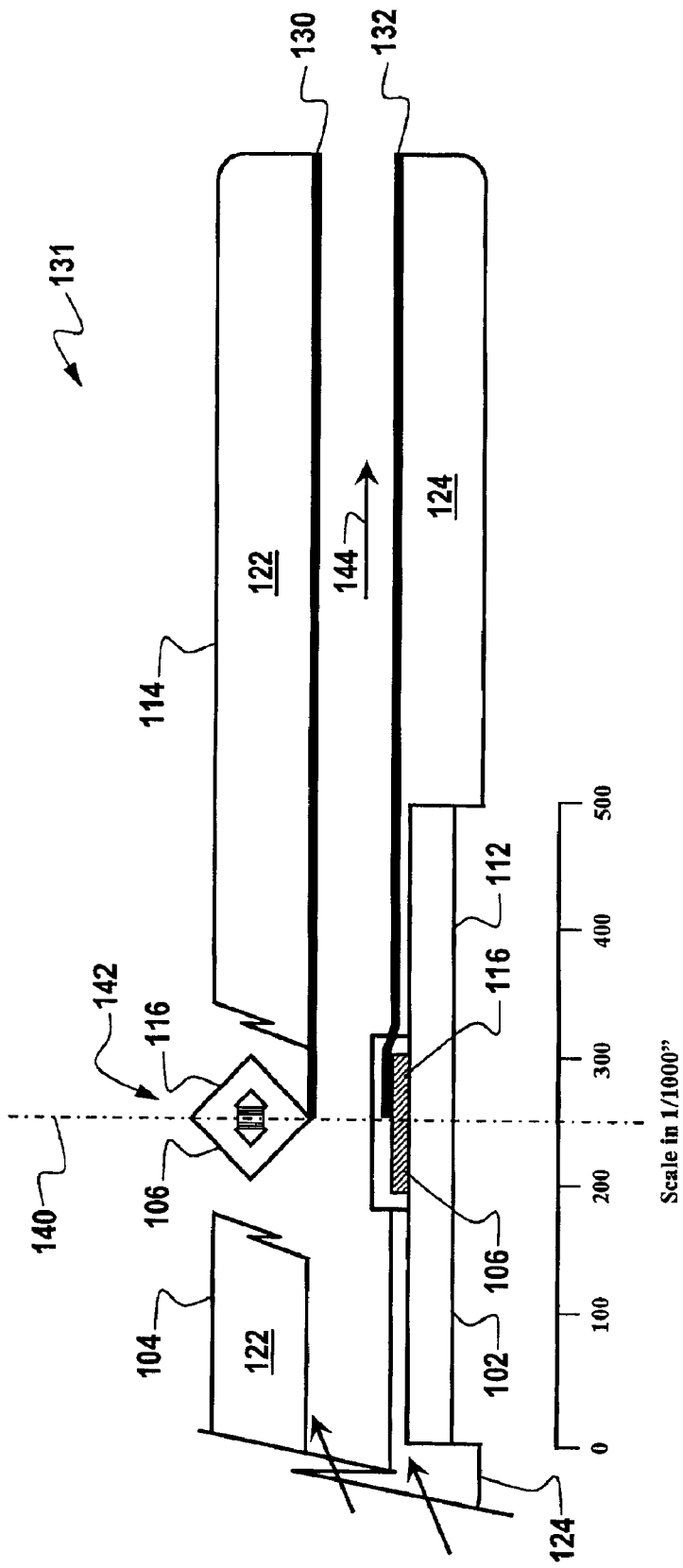
FIG. 3 illustrates a side sectional view of an improved flow channel block with an inserted core, in accordance with a preferred embodiment of the present invention.

FIG. 3 illustrates a side cross-sectional view 131 of an improved flow channel block with an inserted core, in accordance with a preferred embodiment of the present invention. The left side of view 131 further illustrates a side-sectional view of the prior art configuration illustrated in FIG. 1, while the right side illustrates the position of the core tube 118. Note that in FIGS. 1 to 3 analogous or like parts are generally indicated by identical reference numerals. For example, flow channel block 104 of FIG. 1 is analogous to flow channel block 114 of FIG. 2. Thus, as indicated in view 131 of FIG. 3, walls 122 and 124 form walls of flow channel blocks 104 and 114.

FIG. 3 is included herein primarily to highlight the differences between the prior art configuration depicted in FIG. 1 and the improved flow channel block design illustrated in FIG. 2. A dashed line 140 in FIG. 3 indicates a separation point between the prior art design of FIG. 1 and the improved design of FIG. 2. Thus, half of sensor chips 106 and 116 are illustrated in FIG. 3, along with half of substrates 102 and 112. A chip top view 142 is also indicated, showing respective halves of sensor chips 106 and 116. As indicated above, walls 122 and 124 form walls of flow channel blocks 104 and 114. Both flow channel blocks 104 and 114 include walls 122 and 124. Walls 122 and 124 are indicated on both sides of dashed line 140. An arrow 144 indicates a flow of fluid through channel 111 and 121. Walls 130 and 132 of inserted core tube 118 of FIG. 2 are also depicted in FIG. 3.

As explained previously, the wall thickness of the tube removes the sensing chip surface from direct contact with the fluid by a distance corresponding to that thickness, thus desensitizing the sensor to flow changes. This effect can be minimized and possibly balanced by increasing the temperature of the heater temperature above an ambient level, and additionally by designing the wall thickness at the sensor chip contact surface to be as small as possible. Note that even with the use of TTW contacts, the suggested use of a core pipe, whether left in place or not after bonding the "clear plastic" part with the "alumina", reduces flow noise and the risk of leakage or corrosion and enables the application of higher heater temperatures, which also leads to higher sensor temperatures and reduced offsets. Note that as utilized herein, the term "bonding" generally connotes electrical contacting with the wire bonds (e.g., FWB or TTW), while the term "fastening" generally connotes mechanical securing elements and techniques thereof.

In prior art devices and systems, companies such as for example, Unit Instruments, Emerson Inc. and others, have marketed mass flow controllers based on thermal flow sensors with macroscopic core tubes of stainless steel for decades. Such devices typically feature the heater and sensing elements in the form of wire windings around the core metal tube. This fabrication approach, however, can result in large, slow-responding and costly sensors and is generally an ineffective solution.

Improved flow sensors, including the overall structures depicted in FIGS. 2 and 3 can be thus designed, especially as the diameter of the core tube decreases, thereby resulting in more favorable surface-to-volume tube ratios. In the embodiment illustrated in FIG. 2, for example, an approximately 0.061" OD Teflon® tubing (i.e., normally used as wire-insulation) can be threaded through the "clear plastic" flow channel 121 cross-sectionally at the sensor chip 116. Either epoxy or RTV can then be injected via a syringe hole towards the chip area until excess spills out, while the unsealed alumina substrate to flow channel block interface remains under vacuum to minimize trapped air bubbles.

Another fabrication technique can also be implemented, in accordance with an another embodiment of the present invention, in which excess adhesive is generally applied to the individual parts prior to joining, evacuating and thereafter bringing the parts together, while squeezing excess adhesive from the bonding surfaces. After curing of the adhesive, the Teflon® core tube can be easily removed, if desired. Measurement of the electrical resistance between the sensing elements and the introduced conductive aqueous salt solution indicates resistances between an initial $\geq 200$ M$\Omega$ and subsequently after several days, $\geq 30$ M$\Omega$, with the Teflon® tube removed. No degradation or electrical leakage may be measured if the tube can be left in place.

Figure 4:
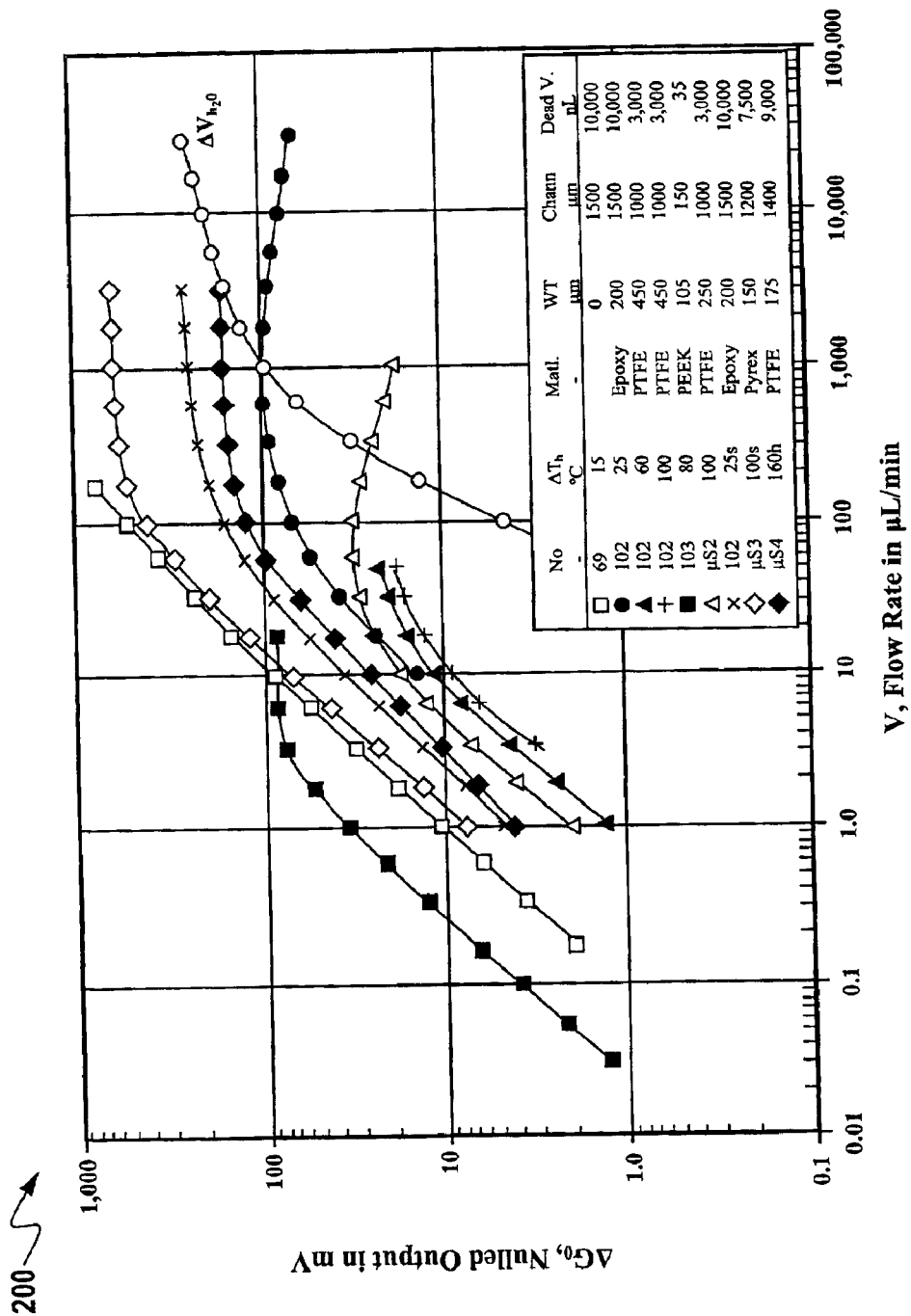
FIG. 4 depicts a graph illustrating the performance of thermal flow sensors with salt water at ambient temperature relative to a flow sensor without a core tube, in accordance with a preferred embodiment of the present invention.

FIG. 4 depicts a graph 200 illustrating the performance of flow sensors with salt water at ambient temperature, in accordance with a preferred embodiment of the present invention. FIG. 4 is presented for illustrative and edification purposes only and is thus not considered a limiting feature of the present invention. Graph 200 indicates that measured flow sensor output versus flow for several flow channel configurations and heater temperature values can be obtained. As illustrated in graph 200, flows that occur below 0.5 nL/s are measurable for a smaller core tube of only 150 $\mu$m internal diameter. In such instances, noise levels may be approximately in the 1 mV range, for which no compensation for fluctuations in ambient temperatures may be in place. Those skilled in the art can thus appreciate that graph 200 illustrates a range of data collected over time regarding nulled-output versus flow rate. Graph 200 thus generally illustrates the beneficial influence of lower wall thickness (WT) and higher thermal conductivity materials for the core tube, which increases sensitivity and flow ranges. An example of a higher thermal conductivity material, which may be utilized in association with an embodiment of the present invention, is Pyrex®. (Note that Pyrex® is a registered trademark of the Corning Glass Works Corporation of Corning, N.Y. 14831.) A further explanation of FIG. 4 is thus not necessary.

Figure 5:
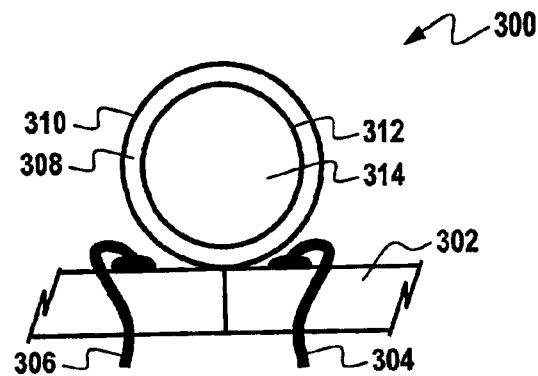
FIG. 5 illustrates a front view of a flow sensor that can be implemented in accordance with a preferred embodiment of the present invention.

FIG. 5 illustrates a front view of a flow sensor 300 that can be implemented in accordance with a preferred embodiment of the present invention. Flow sensor 300 includes an outer surface 310 and an inner surface 312 of a core tube 308 located above a sensing chip 302 with FWBs 306 and 304.

Figure 6:
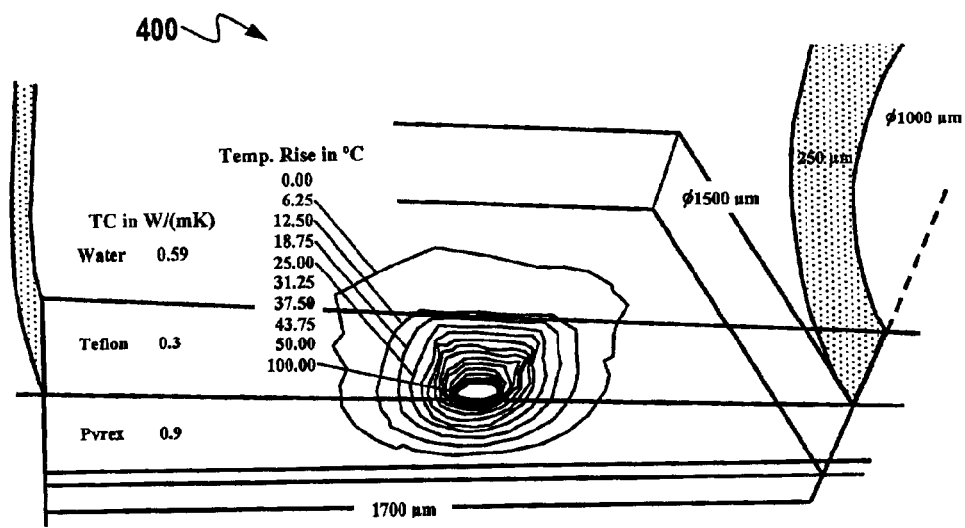
FIG. 6 depicts a cross-sectional perspective view of a temperature field generated by a flow sensor heater, in accordance with a preferred embodiment of the present invention.

FIG. 6 also depicts a cross-sectional side view of a temperature field 400 generated by a flow sensor heater, in accordance with a preferred embodiment of the present invention, whereby the heater can be raised to an exemplary 100° C. above ambient in a plane just 25 $\mu$m off the center with no flow present. FIG. 6 generally illustrates the results of a finite-element computation of the temperature profile of a temperature field near the sensor chip (e.g., sensing chip 302 of FIG. 5 or chip 116 of FIG. 2), thus indicating that even the $\Delta T_h$=6.5° C. isotherm barely penetrates the water and accounts for the loss in sensitivity if the thickness of the flow channel block can be chosen to be as large as, for example, 250 $\mu$m. The use of thin-wall tubes, made of materials of higher thermal conductivity (e.g., approximately 1 W/(mK)) has been demonstrated as a valid approach to minimizing the sensitivity loss.

Figure 7:
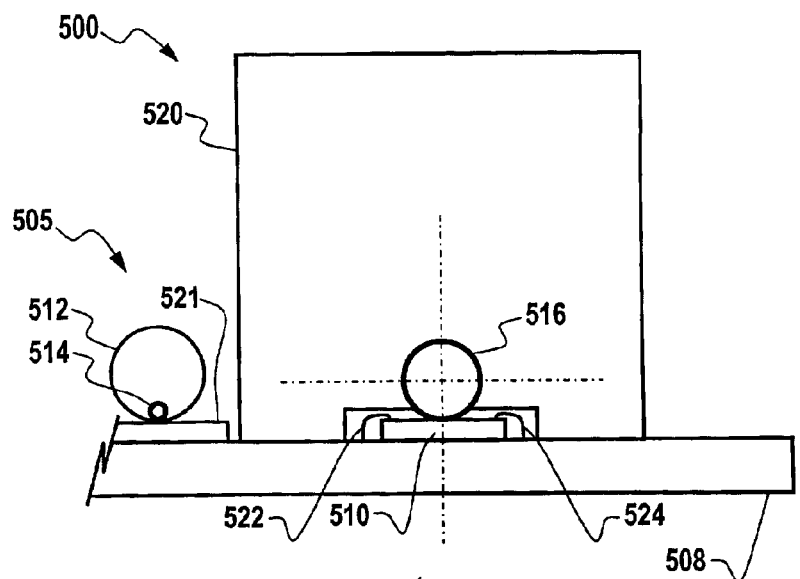
FIG. 7 illustrates a cross-sectional end view of a flow sensor assembly with a glass chip under a Teflon® tube in an epoxy matrix, in accordance with a preferred embodiment of the present invention.

It can be appreciated that modifications to the aforementioned improved sensor configuration (i.e., sensor package) can be made in accordance with the present invention. For example, heat sinking a reference resistance, $R_r$, which is not shown in FIG. 6, to achieve proper control of an associated heater, can be implemented by the skilled when familiar with the SoA. Choosing a thin but strong core tube, made of material with intermediate thermal conductivities is another technique that can be utilized, as described above, in accordance with the apparatus of the present invention. Two other variations and alternative embodiments are further described below FIG. 7 illustrates a cross-sectional end view 500 of a flow sensor assembly 505 with a glass chip 510 under a Teflon® tube 516 in a flow channel body or block 520 (e.g., of about 0.25×0.25" in cross section), which may be implemented in accordance with a preferred embodiment of the present invention, and which can be sized to fit into a Honeywell flow channel housing AWM720. As illustrated in FIG. 7, chip 510 can be located above a substrate 508, which may be composed of alumina, glass, or other substrate material. Chip 510 can be configured to include FWB contacts to substrate 508 via wires 522 and 524. Core tube 516 can be 0.060" in diameter. Additionally, a 0.002" wall thickness can be utilized to sense water flows between <10 to >1000 μL/min. The smaller core tube 514 can be inserted into a groove in rod 512, in place of core tube 516 and may be utilized to sense the flows illustrated in FIG. 4 in a range of, for example, 0.03 μL/min to 3 μL/min. Note that rod 512 is positioned generally above block 521 in FIG. 7. Block 521 is in turn positioned above substrate 508.

Figure 8:
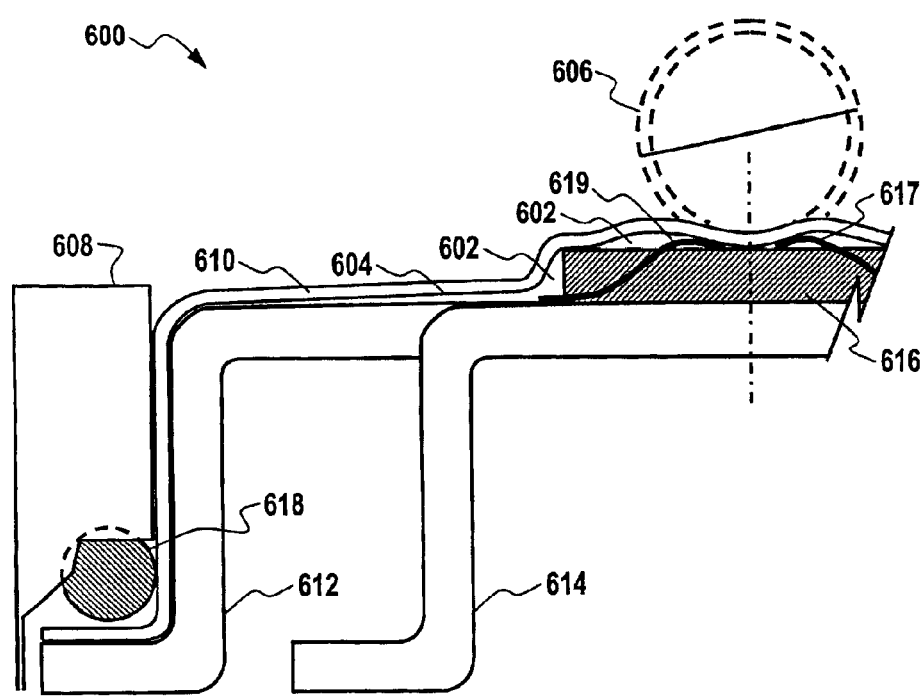
FIG. 8 depicts a graphical diagram illustrating a sensor package for harsh environments applied to large flow channels, or to property measurements, which may be implemented in accordance with a preferred embodiment of the present invention.

FIG. 8 illustrates a sensor package for harsh environments applied to large flow channels, which may be implemented in accordance with a preferred embodiment of the present invention. The sensor chip 616 can be fastened onto a header (e.g., #TO18 614 or #TO5 612) and electrically bonded to one or more associated posts via wires 617 and 619. Instead of exposing the chip surface to the fluid flowing in a channel as large as 0.5" or more, the sensor chip can be protected by film 610, which may be composed of any number of single or laminated, organic or inorganic materials. The thin film 610 is applied to the sensing element, wherein said thin film is applied thinly, thereby enabling reliable, sensitive, low-noise, non-intrusive, non-contaminating, and flow-channel-disposable measurements thereof. In one embodiment, for example, the thin film is applied to the sensing element at a thickness in an inclusive range from about 0.001-in to about 0.010-in.

Note that a virtual channel 606 is depicted in dashed lines in FIG. 8. Such a virtual channel 606 may be, for example, approximately 0.060-in in diameter. As illustrated in FIG. 8, voids 602 may be filled with adhesive such as epoxy. An underside 604 of the polymer film 610 may be "etched" to promote adhesion. An O-ring 618 can be placed around the base of the header to enable sealing against the fluid in the large channel. The header can be fastened by known fastening techniques against the large flow channel block 608, of which only a corner is illustrated in FIG. 8.

Figure 9:
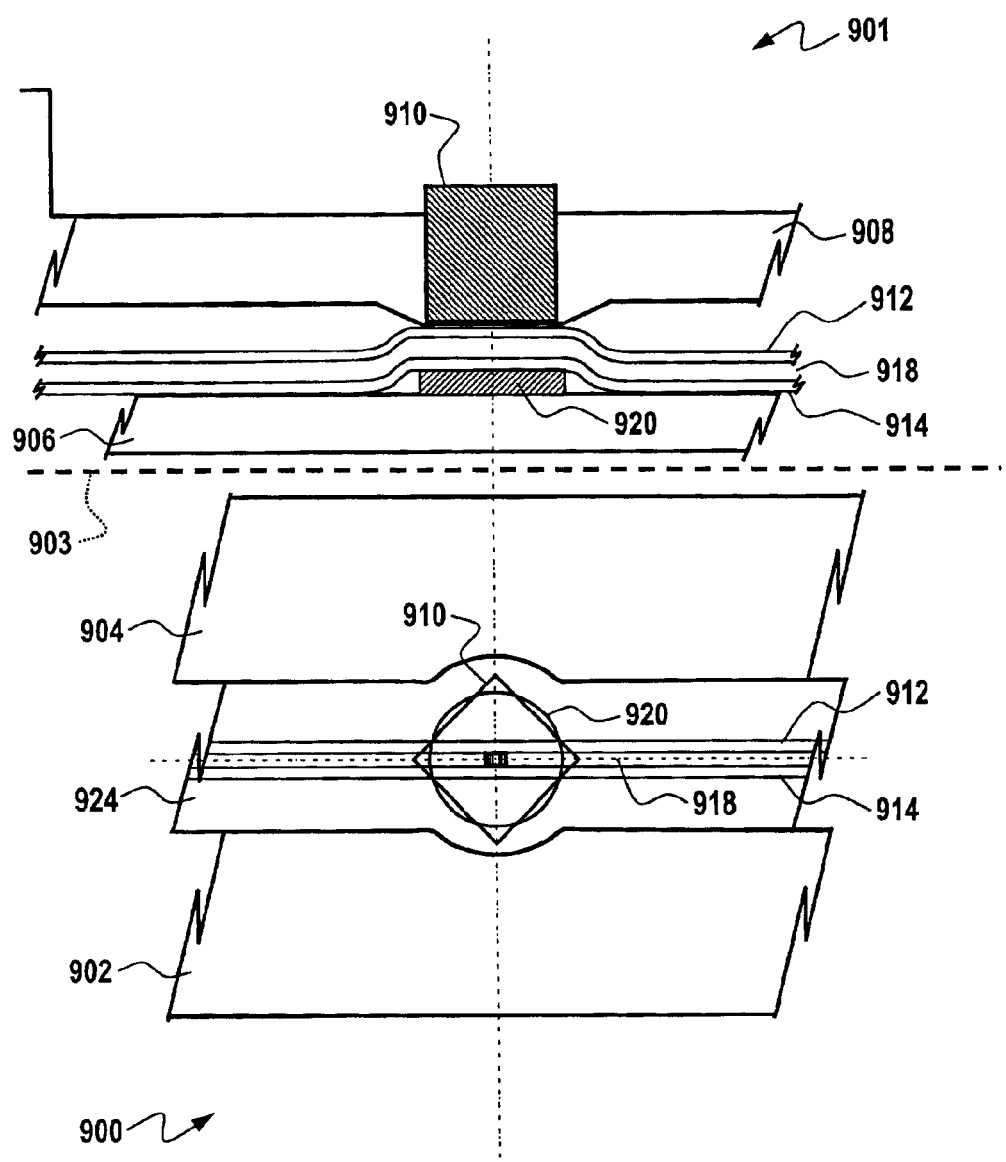
FIG. 9 illustrates a sectional top view and a bottom view of a flow sensor assembly with a small core tube located within walls of a flow channel block thereof, in accordance with a preferred embodiment of the present invention.

FIG. 9 illustrates a sectional top view 901 and a bottom view 900 of a flow sensor assembly with a small core tube 918 (e.g., of ~0.014" outer diameter and 0.006" inner diameter) located within walls 906 and 908 of a flow channel block thereof, in accordance with a preferred embodiment of the present invention. Note that top and bottom views 901 and 900 are separated from one another in FIG. 9 by a dashed line 903. During assembly of the structure illustrated in FIG. 9, an epoxy can be utilized to fill all voids except the inner diameter of core tube 918. Pusher element 910 can be utilized to press core tube walls 912 and 914 onto sensor chip 920 to minimize any void between sensor chip 920 and tube wall 914. This design simplifies for some applications the assembly of small core tubes as explained herein (e.g., the small core tube of FIG. 7). Thus, a simplified yet efficient core tube structure for use with sensor packages for harsh environments can be readily constructed, particularly in view of commercially available parts (e.g., block walls 906, 908, and sensor chip 920, wherein wall 906 can also comprise the circuit bearing substrate).

Figure 10:
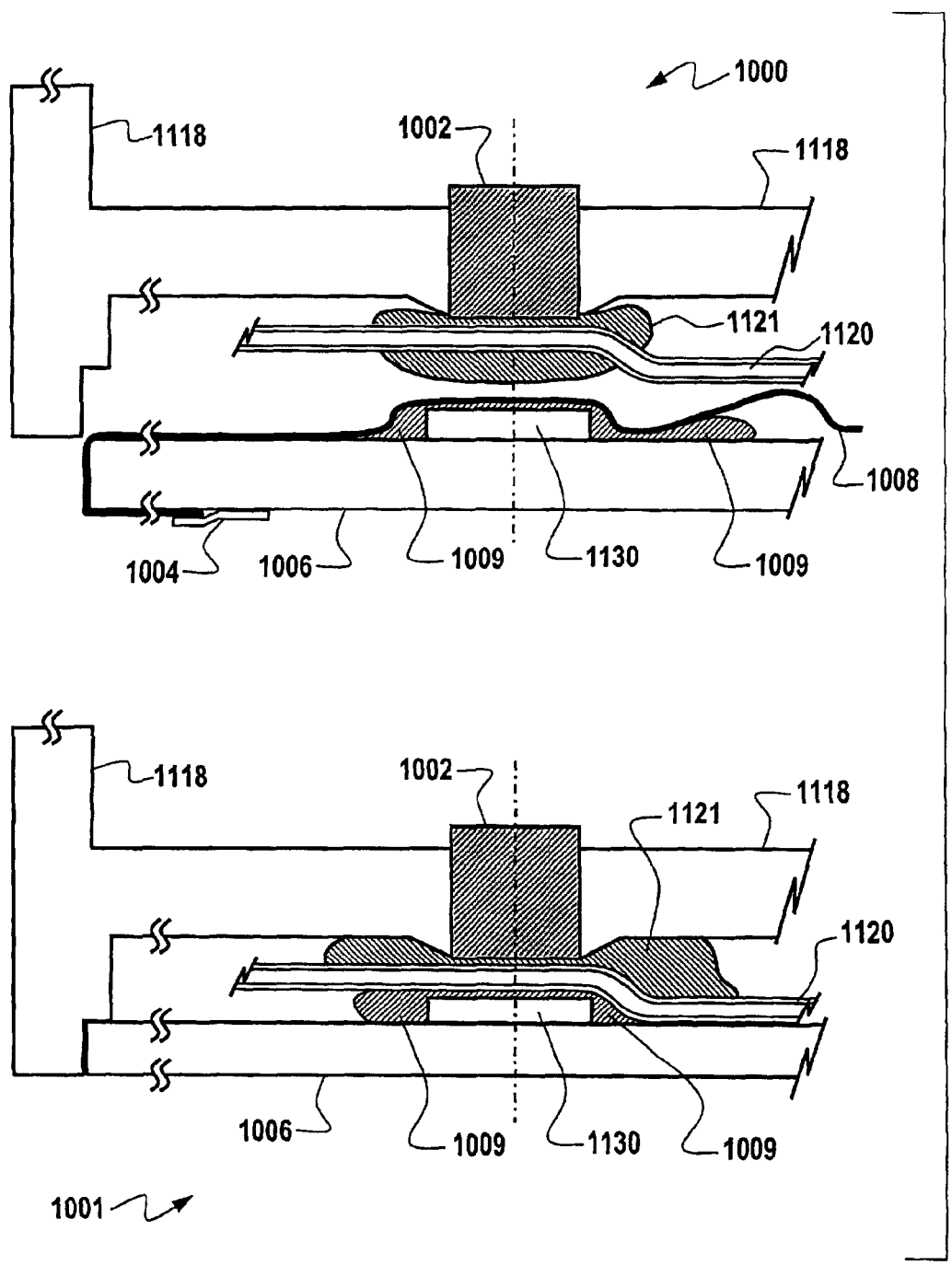
FIG. 10 depicts sectional views of an assembly of a flow channel block and a core tube, in accordance with a preferred embodiment of the present invention.

FIG. 10 depicts sectional views 1000 and 1001 of an assembly of a flow channel block 1119 and a core tube 1120, in accordance with a preferred embodiment of the present invention. View 1000 illustrates an epoxy adhesive 1009 located beneath a film 1008 (e.g., Teflon® tape), which can encase one or more FWBs. During curing and after the insertion of epoxies 1009 and 1121 and assembly thereof, a core tube 1120 can be placed above film 1008 and pressed via a pusher element 1002 onto a sensor chip 1130 and a substrate 1006. Note that pusher element 1002 of FIG. 10 is similar to pusher element 910 of FIG. 9.

By making certain that film 1008 does not adhere to substrate 1006 and sensor chip 1130, nor to epoxy 1121 and flow channel block 1118, one can take the top and bottom halves apart after the epoxy has been cured and remove the film as well. Film 1008 can be formed from a material such as, for example, a Teflon® fluoropolymer or Aclar®. (Note that Aclar® is a registered trademark of the Allied Chemical Corporation of Morris Township, N.J.) The structure indicated in FIG. 10 can thus be fabricated, thereby permitting the perfectly mated top and bottom halves to be reassembled, such that the surface of core tube 1120 contacts the sensing surfaces of sensor chip 1130. After completion of the measurements, the top half of the assembly illustrated in view 1001 of FIG. 10 can be discarded (e.g., it may contain a blood or other biological fluid), without having contaminated the non-disposable and generally more costly part holding the sensor chip 1130 and its calibrated circuit on substrate 1006.

Based on the foregoing it can be appreciated that a number of alternative sensor configurations can be implemented in accordance with the present invention to achieve electrical insulation for liquid or "harsh environment" sensor chips. For example, covering a "to-be-sealed" sensor chip to sense liquid flow or liquid properties with a film that combines high dielectric strength and chemical inertness with hydrophobic properties, whether inorganic or not, may be utilized to achieve such electrical insulation.

Another technique for achieving electrical insulation for liquid or "harsh environment" sensor chips, in accordance with the present invention disclosed herein, involves enlarging and shaping the film as a potting compound of the wire-bonds around the chip, whereby the potting-sealant-adhesive (e.g., epoxy, RTV, etc.) can be shaped by a removable mold core (such as thin tubing or film of fluoropolymer, glass or metal) to reliably provide minimum insulation, while maximizing sensing performance (e.g., higher signal reliability/accuracy due to reduced offsets, lower-noise, longer service life, etc). In such an instance, the tubular mold core tube may be left in place as insulation after potting. The flow sensor itself, according to the present invention disclosed herein, thus can be exposed to the fluid, because the core tube (i.e., core flow tube) can be removed after using it to mold the flow channel. Alternatively, the flow sensor may also be exposed to the fluid if the core tube is left in place. The core tube thus may comprise a disposable flow tube.

In addition, smartly performing the potting enables the fabrication of disposable flow tubes (e.g., for blood or chemical analysis) without disposing of the calibrated sensor and its electronics. Additionally, a constriction in the cross section of the core tube can be provided at the site of the sensor chip (e.g., see FIG. 1) to optimize performance at the location of the highest flow velocity (and signal) and governing pressure drop (i.e., to minimize overall ΔP).

Furthermore, the tube and the flat substrate can be replaced by a flat film (e.g. 20–100 μm thick Teflon®) wrapped or shrunk around a header such as, for example, a TO5 or TO18, and sealed by an O-ring 618 as shown in FIG. 8. Finally, as indicated previously, heat sinking the reference resistance, $R_r$, so that it does not heat up and accidentally drive the heater temperature too high and boil the liquid can be utilized to achieve electrical insulation for liquid or "harsh environment" sensor chips. For example, a small metallic thermal conductor may be utilized, which can be epoxied onto the $R_r$ and increase its heat exchange surface in a direction away from heater resistance, $R_h$.

The flow sensor package disclosed herein offers several advantages over prior art liquid flow sensor packaging approaches. For example, the application of reliably controlling the thickness of the insulating "layer" can eliminate electrical leakages and the risk of electrical shorts. This controlled thickness also enables the application of larger voltages to the sensor heating elements, thus higher heater temperatures, and thus leads to larger output signals, reduced effect of sensor and electronic offsets and without boiling the liquid. The smooth, round flow channel located above the chip cuts down on flow noise while providing the aforementioned benefits, including eliminating the risk of fluid leakage or corrosion and, additionally, providing electrical insulation of the chip contacts. In addition, the smooth, round flow channel inside the molding core (left in place in contact with the sensor chip) can provide a "clean", contaminant-free environment for preserving the maximum fluid cleanliness.

Thus, according to the invention described herein, a sensor can be configured to generally include a flow channel block having a flow channel formed therein and a sensor chip for sensing fluid flow, wherein a fluid in the flow channel surrounds the sensor chip. Alternatively, the sensor chip can be fastened at one side to a substrate and on another side of the substrate to a core tube inserted into the flow channel. This core tube provides electrical insulation and corrosion protection to the sensor chip, reduces flow noise, essentially eliminates the risk of fluid leakage, and maintains the fluid super-clean and contamination-free while improving structural integrity for the thermal measurements derived from the sensor chip. The use of such a core tube configuration also can protect the sensor from corrosion, radioactive or bacterial contamination, deposits, overheating, or freeze-ups. Such a core tube configuration also enables the core tube to be detachable and disposable, without requiring the replacement of the more costly sensor chip and its associated electronics. The present invention can be used in glucose monitoring, laboratory on a chip, drug delivery, cytometer, fluid flow, dialysis, infusion, and other applications. Further, the present invention is applicable to microfluidics and flow sensing applications that need to measure liquids, condensing air or contaminated air. In some embodiments, the present invention can be configured in an isolated mode wherein the media to be sensed does not touch the sensor. In other embodiments, the present invention can be configured in a direct contact mode wherein the media to be sensed touches the sensor.

The embodiments and examples set forth herein are presented to best explain the present invention and its practical application and to thereby enable those skilled in the art to make and utilize the invention. Those skilled in the art, however, will recognize that the foregoing description and examples have been presented for the purpose of illustration and example only. Other variations and modifications of the present invention will be apparent to those of skill in the art, and it is the intent of the appended claims that such variations and modifications be covered. The description as set forth is not intended to be exhaustive or to limit the scope of the invention. Many modifications and variations are possible in light of the above teaching without departing from the scope of the following claims. It is contemplated that the use of the present invention can involve components having different characteristics. It is intended that the scope of the present invention be defined by the claims appended hereto, giving full cognizance to equivalents in all respects.

What is claimed is:

1. A system for detecting fluids in harsh environments, said system comprising:
    a flow channel block having a flow channel formed therein;
    a microsensor chip for sensing fluid flow, wherein said microsensor chip is located proximate to said flow channel of said flow channel block and wherein said microsensor chip comprises a thermal microsensor that includes at least one sensing element for sensing a fluid parameter based on heat transfer and thermal conductivity;
    a substrate in communication with said microsensor chip and at least one electrical contact bonded to it by at least one bonding element, wherein said flow channel is connected to said microsensor chip by a material that facilitates heat transfer and which is disposable upon completion of a fluid measurement;
    a disposable core tube for molding said flow channel, wherein said disposable flow core tube possesses walls thereof and is removably located within said flow channel block to thereby permit detection of liquid flow in harsh environments through said walls of said core tube; and
    wherein said walls of said disposable core tube comprise a wall thickness that removes said surface of said microsensor chip from direct contact with said fluid by a distance corresponding to said wall thickness.

2. The system of claim 1 further comprising a thin film applied to said at least one sensing element, wherein said thin film is applied thinly and comprises a self-supporting layer.

3. The sensor of claim 2 wherein said thin film layer is laminated with an electrical insulating material to provide hermetic sealing thereof.

4. The sensor of claim 1 wherein said microsensor chip is exposed to a fluid following a molding of said flow channel via said disposable core tube.

5. The sensor of claim 1 wherein said microsensor chip is shielded from a fluid when said disposable core tube is left in place within said flow channel block and wherein said substrate comprises silicon.

6. A system for detecting fluid in harsh environments, said system comprising:
    a flow channel block having a flow channel formed therein, wherein said flow channel block is configured in a shape of tube, thereby permitting said flow channel block to comprise a flow tube;
    a microsensor chip for sensing fluid flow, wherein said microsensor chip is located proximate to said flow channel of said flow channel block and wherein said microsensor chip comprises a thermal microsensor that includes at least one sensing element for sensing a fluid parameter based on heat transfer and thermal conductivity;
    a thin film applied to said at least one sensing element, wherein said thin film is applied thinly;
    a substrate comprising glass, wherein said substrate communicates with said microsensor chip and at least one electrical contact bonded to it by at least one bonding element, wherein said removable flow channel is removably connected to said microsensor chip by a material that facilitates heat transfer and which is disposable upon completion of a measurement of a fluid;

a disposable core tube for molding said flow channel, wherein said disposable core tube possesses walls thereof and is located within said flow channel block to thereby permit detection of liquid flow in harsh environments through said walls of said disposable core tube;

wherein said microsensor chip is exposed to said fluid following a molding of said flow channel via said core tube, if said disposable core tube is removed from said flow channel block; and wherein said walls of said core tube possess a wall thickness that prevents a surface of said microsensor chip from direct contact with a fluid flowing through said core tube by a distance corresponding to said wall thickness, if said disposable core tube remains within said flow channel block.

7. The system of claim 6 wherein said disposable core tube comprises a constriction in a cross section of said disposable core tube at said microsensor chip.

8. The system of claim 6 wherein said disposable core tube and said substrate are replaceable by a flat film wrapped about a header and sealed by an O-ring to provide thermal conductivity measurement sensor capabilities thereof, in a zero forced-convection environment.

9. The system of claim 6 wherein a thickness of said thin film applied to said at least one sensing element is in an inclusive range of approximately 0.0001-in to 0.010-in.

10. The system of claim 9 wherein said thin film comprises a self-supporting layer.

11. The system of claim 10 further comprising an electrical insulating material laminated over said thin film to provide hermetic sealing thereof.

12. The system of claim 11 wherein said electrical insulating material comprises a polymeric material.

13. A system for detecting fluids in harsh environments, said system comprising:

a flow channel block having a flow channel formed therein;

a microsensor chip for sensing fluid flow, wherein said microsensor chip is located proximate to said flow channel of said flow channel block and wherein said microsensor chip comprises a thermal microsensor that includes at least one sensing element for sensing a fluid parameter based on heat transfer and thermal conductivity;

a substrate in communication with said microsensor chip and at least one electrical contact bonded to it by at least one bonding element, wherein said flow channel is connected to said microsensor chip by a material that facilitates heat transfer and which is disposable upon completion of a fluid measurement; and a disposable core tube for molding said flow channel, wherein said disposable flow core tube possesses walls thereof and is removably located within said flow channel block to thereby permit detection of liquid flow in harsh environments through said wails of said core tube; and wherein said microsensor chip is shielded from a fluid when said disposable core tube is left in place within said flow channel block and wherein said substrate comprises silicon.

14. The system of claim 13 further comprising a thin film applied to said at least one sensing element, wherein said thin film is applied thinly and comprises a self-supporting layer.

15. The sensor of claim 14 wherein said thin film layer is laminated with an electrical insulating material to provide hermetic sealing thereof.

16. The sensor of claim 13 wherein said microsensor chip is exposed to a fluid following a molding of said flow channel via said disposable core tube.

* * * * *